United States Patent [19]
Robinson

[11] Patent Number: 6,107,337
[45] Date of Patent: Aug. 22, 2000

[54] ARYLSULFONYLAMINO HYDROXAMIC ACID DERIVATIVES

[75] Inventor: Ralph P. Robinson, Gales Ferry, Conn.

[73] Assignee: Pfizer Inc., New York, N.Y.

[21] Appl. No.: 09/130,922

[22] Filed: Aug. 6, 1998

[51] Int. Cl.[7] ............... A61K 31/35; A61K 31/216; A61K 31/50; A61K 31/5375
[52] U.S. Cl. ............... 514/530; 564/90; 564/91; 564/89; 514/237.5; 514/238.2; 514/255; 514/459; 514/538; 514/539; 514/542; 514/562; 514/602; 514/604; 514/824; 514/921; 544/160; 544/391; 544/402; 549/424; 560/13; 562/430
[58] Field of Search ............... 514/238.2, 255, 514/538, 539, 562, 602, 604, 237.5, 459, 530, 542, 824, 921; 562/430; 560/13; 564/89, 90, 91; 544/160, 402, 391; 549/424

[56] References Cited

FOREIGN PATENT DOCUMENTS

| 95/35276 | 12/1995 | WIPO . |
| 96/27583 | 9/1996 | WIPO . |
| 97/05865 | 2/1997 | WIPO . |

*Primary Examiner*—Peter O'Sullivan
*Attorney, Agent, or Firm*—Peter C. Richardson; Paul H. Ginsburg; Seth H. Jacobs

[57] ABSTRACT

A compound of the formula

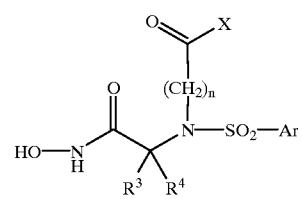

I wherein n, X, $R^3$, $R^4$ and Ar are as defined above, useful in the treatment of a condition selected from the group consisting of arthritis, cancer, tissue ulceration, restenosis, periodontal disease, epidermolysis bullosa, scleritis, bone resorption, loosening of artificial joint implants, atherosclerosis, multiple sclerosis, occular angiogenisis and other diseases characterized by matrix metalloproteinase activity, AIDS, sepsis, septic shock and other diseases involving the production of TNF.

24 Claims, No Drawings

ARYLSULFONYLAMINO HYDROXAMIC ACID DERIVATIVES

This application claims priority under 35 U.S.C. §1.119 (e) of provisional application Ser. 60/055,208, filed Aug. 8, 1997.

BACKGROUND OF THE INVENTION

The present invention relates to arylsulfonylamino hydroxamic acid derivatives. These compounds are inhibitors of matrix metalloproteinases or the production of tumor necrosis factor (hereinafter also referred to as TNF) and as such are useful in the treatment of a condition selected from the group consisting of arthritis, cancer, tissue ulceration, restenosis, periodontal disease, epidermolysis bullosa, scleritis, bone resorption, loosening of artificial joint implants, atherosclerosis, multiple sclerosis, occular angiogenisis (for example macular degeneration and other diseases characterized by matrix metalloproteinase activity, AIDS, sepsis, septic shock and other diseases involving the production of TNF.

This invention also relates to a method of using such compounds in the treatment of the above diseases in mammals, especially humans, and to the pharmaceutical compositions useful therefor.

There are a number of enzymes which effect the breakdown of structural proteins and which are structurally related metalloproteases. Matrix-degrading metalloproteinases, such as gelatinase, stromelysin and collagenase, are involved in tissue matrix degradation (e.g. collagen collapse) and have been implicated in many pathological conditions involving abnormal connective tissue and basement membrane matrix metabolism, such as arthritis (e.g. osteoarthritis and rheumatoid arthritis), tissue ulceration (e.g. corneal, epidermal and gastric ulceration), abnormal wound healing, periodontal disease, bone disease (e.g. Paget's disease and osteoporosis), tumor metastasis or invasion, as well as HIV-infection (*J. Leuk. Biol.*, 52 (2): 244–248, 1992).

Tumor necrosis factor is recognized to be involved in many infectious and auto-immune diseases (W. Friers, *FEBS Letters*, 1991, 285, 199). Furthermore, it has been shown that TNF is the prime mediator of the inflammatory response seen in sepsis and septic shock (C. E. Spooner et al., *Clinical Immunology and Immunopathology*, 1992, 62 S11).

SUMMARY OF THE INVENTION

The present invention relates to a compound of the formula

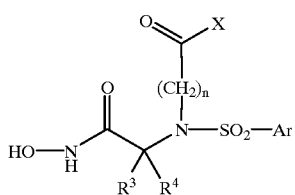

I or the pharmaceutically acceptable salts thereof, wherein
n is an interger from 1 to 6;
X is hydroxy, $(C_1-C_6)$alkoxy or $NR^1R^2$ wherein $R^1$ and $R^2$ are each independently selected from the group consisting of hydrogen, $(C_1-C_6)$alkyl, piperidyl, $(C_1-C_6)$alkylpiperidyl, $(C_6-C_{10})$arylpiperidyl, $(C_2-C_9)$heteroarylpiperidyl, $(C_6-C_{10})$aryl$(C_1-C_6)$ alkylpiperidyl, $(C_2-C_9)$heteroaryl$(C_1-C_6)$ alkylpiperidyl, $(C_1-C_6)$acylpiperidyl, $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_6-C_{10})$aryl $(C_6-C_{10})$aryl, $(C_6-C_{10})$aryl$(C_6-C_{10})$aryl$(C_1-C_6)$ alkyl, $(C_3-C_6)$cycloalkyl, $(C_3-C_6)$cycloalkyl $(C_1-C_6)$alkyl, $R^5(C_2-C_6)$alkyl, $(C_1-C_5)$alkyl$(CHR^5)$ $(C_1-C_6)$alkyl, wherein $R^5$ is hydroxy, $(C_1-C_6)$ acyloxy, $(C_1-C_6)$alkoxy, piperazinyl, $(C_1-C_6)$ acylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$ alkylsulfoxyl, $(C_6-C_{10})$arylsulfoxyl, amino, $(C_1-C_6)$ alkylamino, $((C_1-C_6)$alkyl$)_2$amino, $(C_1-C_6)$ acylpiperazinyl, $(C_1-C_6)$alkylpiperazinyl, $(C_6-C_{10})$ aryl$(C_1-C_6)$alkylpiperazinyl, $(C_2-C_9)$heteroaryl $(C_1-C_6)$alkylpiperazinyl, morpholinyl, thiomorpholinyl, piperidinyl or pyrrolidinyl; $R^6(C_1-C_6)$alkyl, $(C_1-C_5)$alkyl$(CHR^6)(C_1-C_6)$alkyl, wherein $R^6$ is piperidyl, $(C_1-C_6)$alkylpiperidyl, $C_6-C_{10})$arylpiperidyl, $(C_6-C_{10})$aryl$(C_1-C_6)$ alkylpiperidyl, $(C_2-C_9)$heteroarylpiperidyl or $(C_2-C_9)$heteroaryl$(C_1-C_6)$alkylpiperidyl; and $CH(R^7)COR^8$, wherein $R^7$ is hydrogen, $(C_1-C_6)$ alkyl, $(C_6-C_{10})$aryl$(C_1-C_6)$alkyl, $(C_2-C_9)$heteroaryl $(C_1-C_6)$alkyl, $(C_1-C_6)$alkylthio$(C_1-C_6)$alkyl, $(C_6-C_{10})$arylthio$(C_{1-6})$alkyl, $(C_1-C_6)$alkylsulfinyl $(C_1-C_6)$alkyl, $(C_6-C_{10})$arylsulfinyl$(C_1-C_6)$alkyl, $(C_1-C_6)$alkylsulfonyl$(C_1-C_6)$alkyl, $(C_6-C_{10})$ arylsulfonyl$(C_1-C_6)$alkyl, hydroxy$(C_1-C_6)$alkyl, amino$(C_1-C_6)$alkyl, $(C_1-C_6)$alkylamino$(C_1-C_6)$ alkyl, $((C_1-C_6)$alkyl$)_2$amino$(C_1-C_6)$alkyl, $R^9R^{10}NCO(C_1-C_6)$alkyl or $R^9OCO(C_1-C_6)$alkyl wherein $R^9$ and $R^{10}$ are each independently selected from the group consisting of hydrogen, $(C_1-C_6)$ alkyl, $(C_6-C_{10})$aryl$(C_{1-6})$alkyl and $(C_2-C_9)$ heteroaryl$(C_1-C_6)$alkyl; and $R^8$ is $R^{11}O$ or $R^{11}R^{12}N$, wherein $R^{11}$ and $R^{12}$ are each independently selected from the group consisting of hydrogen, $(C_1-C_6)$ alkyl, $(C_6-C_{10})$aryl$(C_1-C_6)$alkyl and $(C_2-C_9)$ heteroaryl$(C_1-C_6)$alkyl;
or $R^1$ and $R^2$, or $R^9$ and $R^{10}$, or $R^{11}$ and $R^{12}$ may be taken together to form an azetidinyl, pyrrolidinyl, morpholinyl, thiomorpholinyl, indolinyl, isoindolinyl, piperazinyl, tetrahydroquinolinyl, tetrahydroisoquinolinyl, $(C_1-C_6)$acylpiperazinyl, $(C_1-C_6)$alkylpiperazinyl, $(C_6-C_{10})$arylpiperazinyl, $(C_2-C_9)$heteroarylpiperazinyl or a bridged diazabicycloalkyl ring selected from the group consisting of

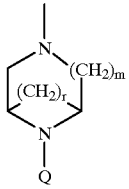

a

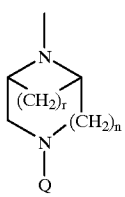

b

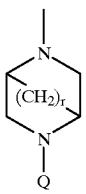

c

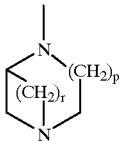

d

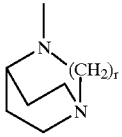

e

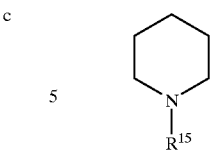

wherein r is 1, 2 or 3;
m is 1 or 2;
p is 0 or 1;
Q is hydrogen, $(C_1-C_3)$alkyl or $(C_1-C_6)$acyl;
$R^3$ and $R^4$ are each independently selected from the group consisting of hydrogen, $(C_1-C_6)$alkyl, trifluoromethyl, trifluoromethyl$(C_1-C_6)$alkyl, $(C_1-C_6)$alkyl(difluoromethylene), $(C_1-C_3)$alkyl (difluoromethylene)$(C_1-C_3)$alkyl, $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_6-C_{10})$aryl $(C_6-C_{10})$aryl, $(C_6-C_{10})$aryl$(C_6-C_{10})$aryl$(C_1-C_6)$ alkyl, $C_3-C_6)$cycloalkyl, $(C_3-C_6)$cycloalkyl$(C_1-C_6)$ alkyl, hydroxy$(C_1-C_6)$alkyl, $(C_1-C_6)$acyloxy$(C_{1-6})$ alkyl, $(C_1-C_6)$alkoxy$(C_1-C_6)$alkyl, piperazinyl $(C_1-C_6)$alkyl, $(C_1-C_6)$acylamino$(C_1-C_6)$alkyl, piperidyl, $(C_1-C_6)$alkylpiperidyl, $(C_6-C_{10})$aryl $(C_1-C_6)$alkoxy$(C_1-C_6)$alkyl, $(C_2-C_9)$heteroaryl $(C_1-C_6)$alkoxy$(C_1-C_6)$alkyl, $(C_1-C_6)$alkylthio $(C_1-C_6)$alkyl, $(C_6-C_{10})$arylthio$(C_1-C_6)$alkyl, $(C_1-C_6)$alkylsulfinyl$(C_1-C_6)$alkyl, $(C_6-C_{10})$ arylsulfinyl$(C_1-C_6)$alkyl, $(C_1-C_6)$alkylsulfonyl $(C_1-C_6)$alkyl, $(C_6-C_{10})$arylsulfonyl$(C_1-C_6)$alkyl, amino$(C_1-C_6)$alkyl, $(C_1-C_6)$alkylamino$(C_1-C_6)$ alkyl, $((C_1-C_6)$alkyl$)_2$amino$(C_1-C_6)$alkyl, $R^{13}CO$ $(C_1-C_6)$alkyl wherein $R^{13}$ is $R^{20}O$ or $R^{20}R^{21}N$ wherein $R^{20}$ and $R^{21}$ are each independently selected from the group consisting of hydrogen, $(C_1-C_6)$ alkyl, $(C_6-C_{10})$aryl$(C_1-C_6)$alkyl or $(C_2-C_9)$ heteroaryl$(C_1-C_6)$alkyl; or $R^{14}(C_1-C_6)$alkyl wherein $R^{14}$ is $(C_1-C_6)$acylpiperazinyl, $(C_6-C_{10})$ arylpiperazinyl, $(C_2-C_9)$heteroarylpiperazinyl, $(C_1-C_6)$alkylpiperazinyl, $(C_6-C_{10})$aryl$(C_1-C_6)$ alkylpiperazinyl, $(C_2-C_9)$heteroaryl$(C_1-C_6)$ alkylpiperazinyl, morpholinyl, thiomorpholinyl, piperidinyl, pyrrolidinyl, piperidyl, $(C_1-C_6)$ alkylpiperidyl, $(C_6-C_{10})$arylpiperidyl, $(C_2-C_9)$ heteroarylpiperidyl, $(C_6-C_{10})$aryl$(C_1-C_6)$ alkylpiperidyl, $(C_2-C_9)$heteroaryl$(C_1-C_6)$ alkylpiperidyl or $(C_1-C_6)$acylpiperidyl;

or $R^3$ and $R^4$, or $R^{20}$ and $R^{21}$ may be taken together to form a $(C_3-C_6)$cycloalkyl, oxacyclohexyl, thiocyclohexyl, indanyl or tetralinyl ring or a group of the formula wherein $R^{15}$ is hydrogen, $(C_1-C_6)$acyl, $(C_1-C_6)$ alkyl, $(C_6-C_{10})$aryl$(C_1-C_6)$alkyl, $(C_2-C_9)$heteroaryl $(C_1-C_6)$alkyl or $(C_1-C_6)$alkylsulfonyl; and Ar is $(C_6-C_{10})$aryl$(C_6-C_{10})$aryl;

with the proviso that when either $R^1$ or $R^2$ is $CH(R^7)$ $COR^8$ wherein $R^7$ and $R^8$ are as defined above, the other of $R^1$ or $R^2$ is hydrogen, $(C_1-C_6)$alkyl or benzyl.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is as defined as above.

The term "$(C_6-C_{10})$aryl", as used herein, unless otherwise indicated, includes an organic radical derived from an aromatic hydrocarbon by removal of one hydrogen, such as phenyl or naphthyl, optionally substituted by 1 to 3 substituents selected from the group consisting of fluoro, chloro, trifluoromethyl, $(C_1-C_6)$alkoxy, trifluoromethoxy, difluoromethoxy and $(C_1-C_6)$alkyl.

The term "$(C_2-C_9)$heteroaryl", as used herein, unless otherwise indicated, includes an organic radical derived from an aromatic heterocyclic compound by removal of one hydrogen, such as pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 2 substituents independently selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl.

The term "acyl", as used herein, unless otherwise indicated, includes a radical of the general formula RCO wherein R is alkyl, alkoxy, aryl, arylalkyl or arylalkyloxy and the terms "alkyl" or "aryl" are as defined above.

The term "acyloxy", as used herein, includes O-acyl groups wherein "acyl" is as defined as above.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compound of formula I may have chiral centers and therefore exist in different enantiomeric forms. This invention relates to all optical isomers and stereoisomers of the compounds of formula I and mixtures thereof.

Preferred compounds of formula I include those wherein n is 2.

Other preferred compounds of formula I include those wherein Ar is 4-fluorophenyl-phenyl, 4-chlorophenyl-phenyl or phenyl-phenyl.

Other preferred compounds of formula I include those wherein either $R^3$ or $R^4$ is not hydrogen.

Other preferred compounds of formula I include those wherein n is 1, X is $NR^1R^2$ and either $R^1$ or $R^2$ is not hydrogen.

Other preferred compounds of formula I include those wherein X is hydroxy, Ar is 4-fluorophenyl-phenyl, phenyl-phenyl or 4-chlorophenyl-phenyl and either $R^3$ or $R^4$ is not hydrogen.

Other preferred compounds of formula I include those wherein X is alkoxy, Ar is 4-fluorophenyl-phenyl, phenyl-phenyl or 4-chlorophenyl-phenyl and either $R^3$ or $R^4$ is not hydrogen.

Other preferred compounds of formula I include those wherein Ar is 4-fluorophenyl-phenyl, phenyl-phenyl or 4-chlorophenyl-phenyl and $R^3$ and $R^4$ are taken together to form $(C_3–C_6)$cycloalkanyl, oxacyclohexanyl, thiocyclohexanyl, indanyl or a group of the formula

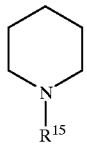

wherein $R^{15}$ is $(C_1–C_6)$acyl, $(C_1–C_6)$alkyl, $(C_6–C_{10})$aryl $(C_1–C_6)$alkyl, $(C_2–C_9)$heteroaryl$(C_{1-6})$alkyl or $(C_{1-6})$alkylsulfonyl.

Other preferred compounds of formula I include those wherein Ar is 4-fluorophenyl-phenyl, phenyl-phenyl or 4-chlorophenyl-phenyl, and $R^3$ and $R^4$ are each $(C_1–C_6)$ alkyl, preferably each of $R^3$ and $R^4$ are methyl.

Other preferred compounds of formula I include those wherein X is hydroxy or $(C_1–C_6)$alkoxy.

Other preferred compounds of formula I include those wherein n is 2, X is $NR^1R^2$ and $R^1$ and $R^2$ are taken together to form a heterocycle selected from piperazinyl and morpholinyl. More preferred compounds of formula I are those wherein Ar is 4-fluorophenyl-phenyl, phenyl-phenyl or 4-chlorophenyl-phenyl.

Specific preferred compounds of formula I include the following:

3-[(4'-fluorobiphenyl-4-sulfonyl)-(1-hydroxycarbamoylcyclopentyl)amino] propionic acid methyl ester, 3-[(4'-fluorobiphenyl-4-sulfonyl)-(1-hydroxycarbamoylcyclopentyl)amino] propionic acid, 3-[(4'-fluorobiphenyl-4-sulfonyl)-(1-hydroxycarbamoyl-1-methyl-ethyl)amino]-propionic acid ethyl ester, and 3-[(4'-fluorobiphenyl-4-sulfonyl)-(1-hydroxycarbamoyl-1-methyl-ethyl)amino]propionic acid.

Other compounds of formula I include the following:

3-[(4'-fluorobiphenyl-4-sulfonyl)-(4-hydroxycarbamoyltetrahydropyran-4-yl)amino] propionic acid, 3-[(4'-fluorobiphenyl-4-sulfonyl)-(4-hydroxycarbamoyltetrahydropyran-4-yl)amino] propionic acid ethyl ester, 3-[(4'-chlorobiphenyl-4-sulfonyl)-(4-hydroxycarbamoyltetrahydropyran-4-yl)amino] propionic acid, 3-[(4'-chlorobiphenyl-4-sulfonyl)-(4-hydroxycarbamoyltetrahydropyran-4-yl)amino] propionic acid ethyl ester, 1-[(4'-fluorobiphenyl-4-sulfonyl)-(3-oxo-3-piperazin-1-ylpropyl)amino]cyclopentanecarboxylic acid hydroxyamide, 4-[(4'-fluorobiphenyl-4-sulfonyl)-(3-oxo-3-piperazin-1-yl-propyl)-amino]tetrahydropyran-4-carboxylic acid hydroxyamide, 1-[(4'-fluorobiphenyl-4-sulfonyl)-(3-morpholin-4-yl-3-oxopropyl)amino]cyclopentanecarboxylic acid hydroxyamide, 2-[(biphenyl-4-sulfonyl)-(3-morpholin-4-yl-3-oxo-propyl)amino]-N-hydroxy-3-methylbutyramide, 1-{(4'-fluoro-biphenyl-4-sulfonyl)-[3-(5-methyl-2,5-diaza-bicyclo[2.2.1]hept-2-yl)-3-oxo-propyl]-amino}-cyclopentanecarboxylic acid hydroxyamide, 4-{(4'-fluorobiphenyl-4-sulfonyl)-[3-(5-methyl-2,5-diazabicyclo[2.2.1]hept-2-yl)-3-oxo-propyl]-amino}tetrahydropyran-4-carboxylic acid hydroxyamide, 3-[(cyclohexylhydroxycarbamoylmethyl)-(4'-fluoro-biphenyl-4-sulfonyl)-amino]propionic acid, and 3-[(cyclohexylhydroxycarbamoylmethyl)-(4'-fluoro-biphenyl-4-sulfonyl)-amino]propionic acid ethyl ester.

The present invention also relates to a pharmaceutical composition for (a) the treatment of a condition selected from the group consisting of arthritis, cancer, tissue ulceration, restenosis, periodontal disease, epidermolysis bullosa, scleritis, bone resorption, loosening of artificial joint implants, atherosclerosis, multiple sclerosis, occular angiogenisis (for example macular degeneration) and other diseases characterized by matrix metalloproteinase activity, AIDS, sepsis, septic shock and other diseases involving the production of tumor necrosis factor (TNF) or (b) the inhibition of matrix metalloproteinases or the production of tumor necrosis factor (TNF) in a mammal, including a human, comprising an amount of a compound of claim 1 or a pharmaceutically acceptable salt thereof, effective in such treatments or inhibition and a pharmaceutically acceptable carrier.

The present invention also relates to a method for the inhibition of (a) matrix metalloproteinases or (b) the production of tumor necrosis factor (TNF) in a mammal, including a human, comprising administering to said mammal an effective amount of a compound of claim 1 or a pharmaceutically acceptable salt thereof.

The present invention also relates to a method for treating a condition selected from the group consisting of arthritis, cancer, tissue ulceration, restenosis, periodontal disease, epidermolysis bullosa, scleritis, bone resorption, loosening of artificial joint implants, atherosclerosis, multiple sclerosis, occular angiogenisis (for example macular degeneration and other diseases characterized by matrix metalloproteinase activity, AIDS, sepsis, septic shock and other diseases involving the production of tumor necrosis factor (TNF) in a mammal, including a human, comprising administering to said mammal an amount of a compound of claim 1 or a pharmaceutically acceptable salt thereof, effective in treating such a condition.

This invention also encompasses pharmaceutical compositions containing and methods of treating or preventing comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

DETAILED DESCRIPTION OF THE INVENTION

The following reaction Schemes illustrate the preparation of the compounds of the present invention. Unless otherwise indicated $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{20}$, $R^{21}$, m, n, p, r, X, Q and Ar in the reaction Schemes and the discussion that follow are defined as above.

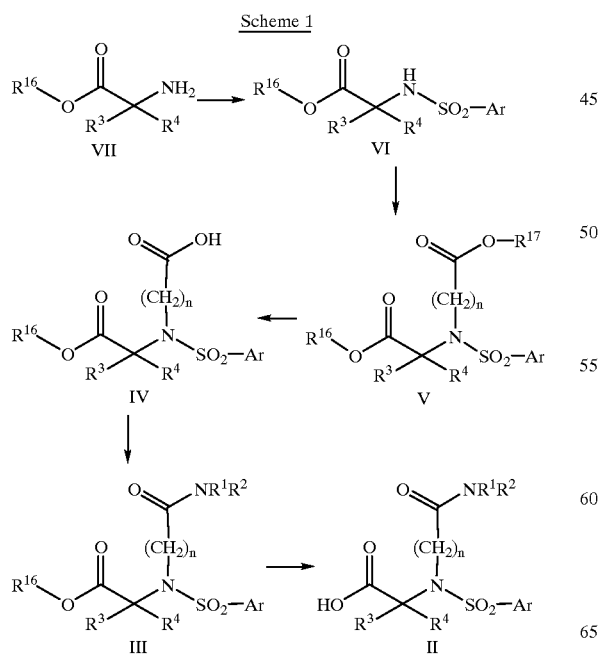

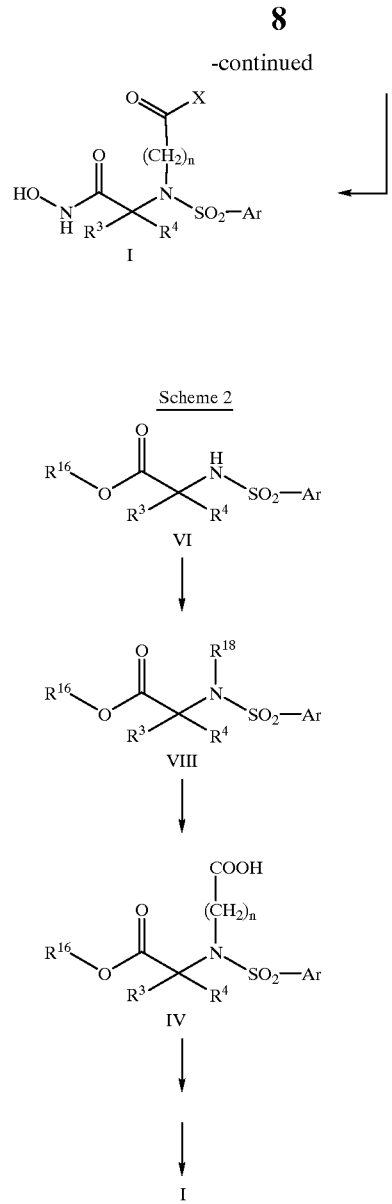

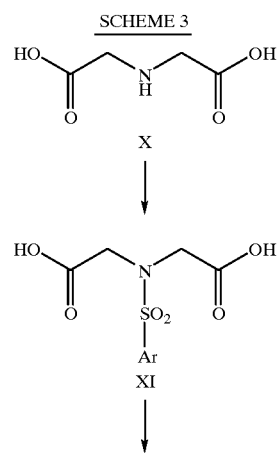

-continued

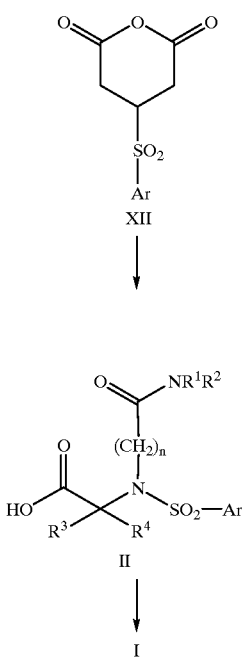

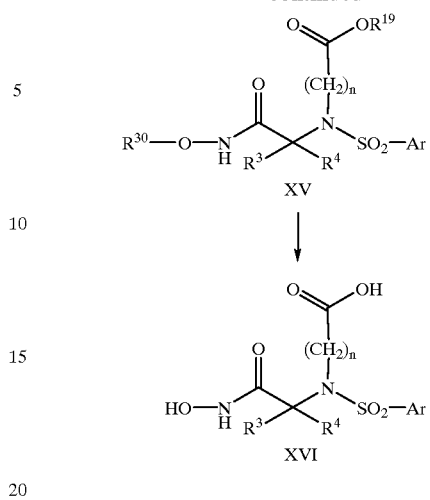

Scheme 1 refers to the preparation of compounds of formula I, wherein X is $NR^1R^2$ and n is 1, 3, 4, 5 or 6, from compounds of the formula VII. Referring to Scheme 1, the amino acid compound of formula VII, wherein $R^{16}$ is $(C_1-C_6)$alkyl, benzyl, allyl or tert-butyl, is converted to the corresponding compound of formula VI by reaction with a reactive functional derivative of an arylsulfonic acid compound, such as an arylsulfonyl chloride, in the presence of a base, such as triethylamine, and a polar solvent, such as tetrahydrofuran, dioxane, water or acetonitrile, preferably a mixture of dioxane and water. The reaction mixture is stirred, at room temperature, for a time period between about 10 minutes to about 24 hours, preferably about 60 minutes.

The arylsulfonyl amino compound of formula VI, wherein $R^{16}$ is $(C_1-C_6)$alkyl, benzyl, allyl or tert-butyl, is converted to the corresponding compound of formula V, wherein n is 1, 3, 4, 5 or 6, by reaction with a reactive derivative of an alcohol of the formula

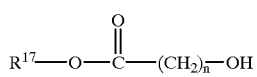

such as the chloride, bromide or iodide derivative, preferably the bromide derivative, wherein the $R^{17}$ protecting group is $(C_1-C_6)$alkyl, benzyl, allyl or tert-butyl, in the presence of a base such as potassium carbonate or sodium hydride, preferably sodium hydride, and a polar solvent, such as dimethylformamide. The reaction mixture is stirred, at room temperature, for a time period between about 60 minutes to about 48 hours, preferably about 18 hours. The $R^{17}$ protecting group is chosen such that it may be selectively removed in the presence of and without loss of the $R^{16}$ protecting group, therefore, $R^{17}$ cannot be the same as $R^{16}$.

Removal of the $R^{17}$ protecting group from the compound of formula V to give the corresponding carboxylic acid of formula IV is carried out under conditions appropriate for that particular $R^{17}$ protecting group in use which will not affect the $R^{16}$ protecting group. Such conditions include; (a) saponification where $R^{17}$ is $(C_1-C_6)$alkyl and $R^{16}$ is tert-butyl, (b) hydrogenolysis where $R^{17}$ is benzyl and $R^{16}$ is tert-butyl or $(C_1-C_6)$alkyl, (c) treatment with a strong acid such as trifluoroacetic acid or hydrochloric acid where $R^{17}$

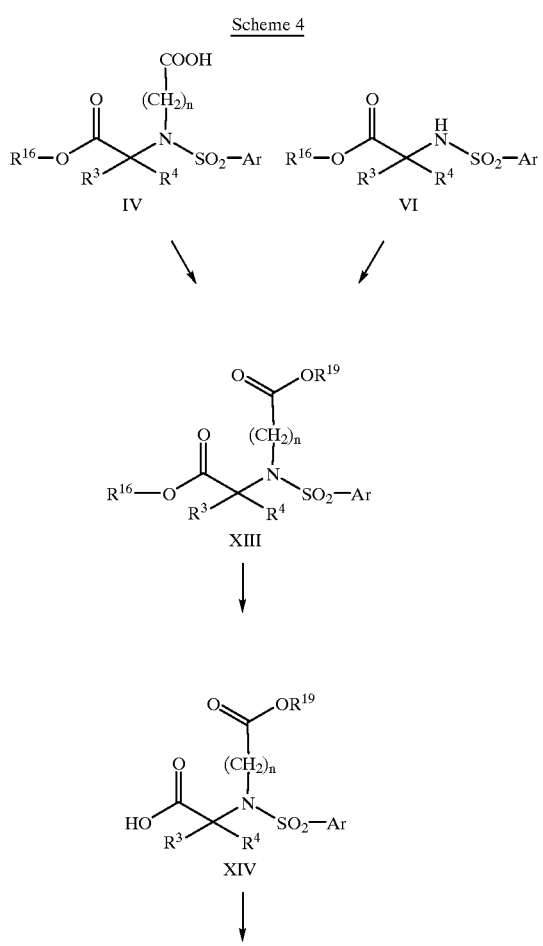

is tert-butyl and $R^{16}$ is $(C_1-C_6)$alkyl, benzyl or allyl, or (d) treatment with tributyltinhydride and acetic acid in the presence of catalytic bis(triphenylphosphine) palladium (II) chloride where $R^{17}$ is allyl and $R^{16}$ is $(C_1-C_6)$alkyl, benzyl or tert-butyl.

The carboxylic acid of formula IV is condensed with an amine, $R^1R^2NH$, or the salt thereof, to give the corresponding amide compound of formula III. The formation of amides from primary or secondary amines or ammonia and carboxylic acids is achieved by conversion of the carboxylic acid to an activated functional derivative which subsequently undergoes reaction with a primary or secondary amine or ammonia to form the amide. The activated functional derivative may be isolated prior to reaction with the primary or secondary amine or ammonia. Alternatively, the carboxylic acid may be treated with oxalyl chloride or thionyl chloride, neat or in an inert solvent, such as chloroform, at a temperature between about 25° C. to about 80° C., preferably about 50° C., to give the corresponding acid chloride functional derivative. The inert solvent and any remaining oxalyl chloride or thionyl chloride is then removed by evaporation under vacuum. The remaining acid chloride functional derivative is then reacted with the primary or secondary amine or ammonia in an inert solvent, such as methylene chloride, to form the amide. The preferred method for the condensation of the carboxylic acid of formula IV with an amine to provide the corresponding amide compound of formula III is the treatment of IV with (benzotriazol-1-yloxy)tris(dimethylamino) phosphonium hexafluorophosphate in the presence of a base, such as triethylamine, to provide the benzotriazol-1-oxy ester in situ which, in turn, reacts with the amine, $R^1R^2NH$, in an inert solvent, such as methylene chloride, at room temperature to give the amide compound of formula III.

Removal of the $R^{16}$ protecting group from the compound of formula III to give the corresponding carboxylic acid of formula II is carried out under conditions appropriate for the particular $R^{16}$ protecting group in use. Such conditions include; (a) saponification where $R^{16}$ is lower alkyl, (b) hydrogenolysis where $R^{16}$ is benzyl, (c) treatment with a strong acid, such as trifluoroacetic acid or hydrochloric acid, where $R^{16}$ is tert-butyl, or (d) treatment with tributyltinhydride and acetic acid in the presence of catalytic bis(triphenylphosphine) palladium (II) chloride where $R^{16}$ is allyl.

The carboxylic acid compound of formula II is converted to the hydroxamic acid compound of formula I by treating II with 1-(3-dimethylaminopropyl)-3-ethylcarbodiimide and 1-hydroxybenztriazole in a polar solvent, such as dimethylformamide, followed by the addition of hydroxylamine to the reaction mixture after a time period between about 15 minutes to about 1 hour, preferably about 30 minutes. The hydroxylamine is preferably generated in situ from a salt form, such as hydroxylamine hydrochloride, in the presence of a base, such as N-methylmorpholine. Alternatively, a protected derivative of hydroxylamine or its salt form, where the hydroxyl group is protected as a tert-butyl, benzyl or allyl ether, may be used in the presence of (benzotriazol-1-yloxy)tris(dimethylamino) phosphonium hexafluorophosphate and a base, such as N-methylmorpholine. Removal of the hydroxylamine protecting group is carried out by hydrogenolysis for a benzyl protecting group or treatment with a strong acid, such as trifluoroacetic acid, for a tert-butyl protecting group. The allyl protecting group may be removed by treatment with tributyltinhydride and acetic acid in the presence of catalytic bis(triphenylphosphine) palladium (II) chloride. N,O-bis(4-methoxybenzyl)hydroxylamine may also be used as the protected hydroxylamine derivative where deprotection is achieved using a mixture of methanesulfonic acid and trifluoroacetic acid.

Scheme 2 refers to the preparation of compounds of the formula I, wherein n is 2, from compounds of the formula VI. Referring to Scheme 2, the arylsulfonylamino compound of formula VI, wherein $R^{16}$ is $(C_1-C_6)$alkyl, benzyl or tert-butyl, is converted to the corresponding compound of formula VIII, wherein $R^{18}$ is 2-propenyl or 3-butenyl, by reacting IX with a reactive functional derivative, such as the halide, preferably the iodide derivative, of 2-propen-1-ol when $R^{18}$ is 2-propenyl or 3-buten-1-ol when $R^{18}$ is 3-butenyl, in the presence of a base, such as potassium carbonate, cesium carbonate or sodium hydride, preferably sodium hydride when $R^{18}$ is 2-propenyl or cesium carbonate when $R^{18}$ is 3-butenyl. The reaction is stirred in a polar solvent, such as dimethylformamide, at room temperature, for a time period between about 2 hours to about 48 hours, preferably about 18 hours.

The compound of formula VIII, wherein $R^{18}$ is 2-propenyl, is converted to the compound of formula IV, wherein n is 2, by reaction with borane-dimethylsulfide complex, followed by immediate oxidation using chromium trioxide in aqueous acetic acid. The oxidative cleavage of terminal olefins to carboxylic acids can be achieved by several methods known in the art. The preferred method for the oxidative cleavage of the compound of formula VIII, wherein $R^{18}$ is 3-butenyl, to obtain the carboxylic acid compound of formula IV is to react VIII with sodium periodate in the presence of a catalytic amount of ruthenium (III) chloride in a mixture of carbon tetrachloride, acetonitrile and water.

Alternatively, the compound of formula VI, wherein $R^{16}$ is benzyl, is converted to the corresponding compound of formula VIII, wherein $R^{18}$ is the group 3-tert-butyl-dimethylsilanyloxypropanyl and $R^{16}$ is benzyl, by reaction with tert-butyl-(halo-propoxy)-dimethylsilane, preferably the iodide derivative, in the presence of a base, such as potassium carbonate, cesium carbonate, potassium hexamethyldisilazide, or sodium hydride, preferably potassium hexamethyldisilazide. The reaction is stirred in a polar solvent, such as dimethylformamide or N-methylpyrrolidin-2-one, at room temperature, for a time period between about 2 hours to about 48 hours, preferably about 18 hours.

The compound of formula VIII, wherein $R^{18}$ is the group 3-tert-butyl-dimethylsilanyloxypropanyl and $R^{16}$ is benzyl, is converted to a carboxylic acid derivative of formula IV by reaction with boron trifluoride-etherate complex to form an intermediate alcohol, followed by immediate oxidation. Specifically, the reaction with boron trifluoride-etherate complex is performed in an inert solvent such as methylene chloride, chloroform, preferably methylene chloride, at room temperature for about 15 minutes to about 4 hours, preferably about one hour. Oxidation of the alcohol is facilitated by using chromium trioxide in aqueous sulfuric acid (Jones Reagent) at about 0° C. for about one to about 6 hours, preferably about 2 hours.

The compounds of formula IV, wherein n is 2, can be converted to compounds of formula I, wherein n is 2 and X is $NR^1R^2$, according to the methods of Scheme 1. The compounds of formula IV, wherein n is 2, can be converted to compounds of formula I, wherein n is 2 and X is hydroxy or $(C_1-C_6)$alkoxy, according to the methods of Scheme 4.

Scheme 3 refers to an alternative method for the synthesis of the hydroxamic acid compound of formula I, wherein n is 1 and $R^3$ and $R^4$ are both hydrogen. Referring to Scheme 3, an iminoacetic acid or a metal or ammonium salt of iminoacetic acid of formula X is reacted with a functional derivative of an arylsulfonic acid compound, such as an arylsulfonyl chloride, at room temperature, in the presence of a suitable base, such as triethylamine, and a polar solvent such as tetrahydrofuran, dioxane, water or acetonitrile, preferably a mixture of dioxane and water, to give the corresponding dicarboxylic acid compound of formula XI. The aforesaid reaction is performed at a temperature of about 20° C. to about 25° C., for a period from about 4 hours to about 36 hours, preferably 24 hours.

The dicarboxylic acid compound of formula XI is dehydrated to give a cyclic anhydride compound of formula XII. The formation of cyclic anhydrides by dehydration of dicarboxylic acids may be achieved by a variety of means. The preferred method for the dehydration of the dicarboxylic acid compound of formula XI to give a cyclic anhydride compound of formula XII is to treat XI with an excess of acetic anhydride at a temperature between about 25° C. to about 80° C., preferably about 60° C. Excess acetic anhydride and acetic acid, a by-product of the reaction, are removed by evaporation under reduced pressure leaving the cyclic anhydride compound of formula XII.

The cyclic anhydride compound of formula XII is reacted, at room temperature, with an amine, $NHR^1R^2$, or a salt of the amine, such as the hydrochloride, in the presence of a base, such as triethylamine, to give the carboxylic acid of formula II, wherein n is 1 and $R^3$ and $R^4$ are both hydrogen. Suitable solvents for the reaction are those that will not react with the starting materials, which include chloroform, methylene chloride and dimethylformamide, preferably methylene chloride.

The compound of formula II is further reacted to give the hydroxamic acid compound of formula I, wherein n is 1 and $R^3$ and $R^4$ are both hydrogen, according to the procedure described above in Scheme 1.

Scheme 4 refers to the preparation of compounds of the formula I, wherein X is hydroxy or $(C_1-C_6)$alkoxy. Referring to Scheme 4, the carboxylic acid compound of formula IV, wherein n is 2, is converted to the corresponding compound of formula XIII, wherein $R^{19}$ is $(C_1-C_6)$alkyl or tert-butyl, by reacting IV with a compound of the formula $$(R^{19}O)_2CHN(CH_3)_2$$

wherein $R^{19}$ is $(C_1-C_6)$alkyl or tert-butyl, in an inert solvent, such as toluene, at a temperature between about 60° C. to about 100° C., preferably about 100° C., for a time period between about 1 hour to about 3 hours, preferably 2 hours.

Alternatively, the carboxylic acid of formula IV is converted into a compound of formula XIII, wherein $R^{19}$ is $(C_1-C_6)$alkyl, by treatment of the free acid with an alkylating agent such as $R^{19}$-L, wherein L is a leaving group such as iodo, bromo, mesylate, or tosylate, preferably iodo, and $R^{19}$ is $(C_1-C_6)$alkyl, with a base, such potassium carbonate or cesium carbonate, preferably potassium carbonate, in a polar solvent such as N,N-dimethylformamide, N-methylpyrrolidin-2-one or tetrahydrofuran, preferably dimethyl formamide, for about 1 to about 24 hours, preferably 16 hours, at about room temperature.

The arylsulfonyl amino compound of formula VI, wherein n is 1, 3, 4, 5 or 6 and $R^{16}$ is $(C_1-C_6)$alkyl, benzyl, allyl or tert-butyl, is converted to the corresponding compound of formula XIII, wherein $R^{19}$ is $(C_1-C_6)$alkyl or tert-butyl, by reacting VI with a reactive derivative of an alcohol of the formula

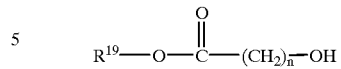

such as the chloride, bromide or iodide derivative, preferably the bromide derivative, wherein $R^{19}$ is $(C_1-C_6)$alkyl or tert-butyl, in the presence of a base such as potassium carbonate or sodium hydride, preferably sodium hydride, and a polar solvent, such as dimethylformamide. The reaction is stirred, at room temperature, for a time period between about 60 minutes to about 48 hours, preferably about 18 hours. The $R^{16}$ protecting group, of the compounds of formulas IV and VI, is chosen such that it may be selectively removed in the presence of and without loss of the $R^{19}$ $(C_1-C_6)$alkyl or tert-butyl group, therefore, $R^{16}$ cannot be the same as $R^{19}$.

Removal of the $R^{16}$ protecting group from the compound of formula XIII to give the corresponding carboxylic acid of formula XIV, wherein n is 1 to 6, is carried out under conditions appropriate for that particular $R^{16}$ protecting group in use which will not affect the $R^{19}$ $(C_1-C_6)$alkyl or tert-butyl group. Such conditions include; (a) saponification where $R^{16}$ is $(C_1-C_6)$alkyl and $R^{19}$ is tert-butyl, (b) hydrogenolysis where $R^{16}$ is benzyl and $R^{19}$ is tert-butyl or $(C_1-C_6)$alkyl, (c) treatment with a strong acid such as trifluoroacetic acid or hydrochloric acid where $R^{16}$ is tert-butyl and $R^{19}$ is $(C_1-C_6)$alkyl, or (d) treatment with tributyltinhydride and acetic acid in the presence of catalytic bis(triphenylphosphine) palladium (II) chloride where $R^{16}$ is allyl and $R^{19}$ is $(C_1-C_6)$alkyl or tert-butyl.

The carboxylic acid of formula XIV is converted to the to the hydroxamic acid compound of formula XV, wherein n is 1 to 6 and $R^{30}$ is hydrogen, by treating XIV with 1-(3-dimethylaminopropyl)-3-ethylcarbodiimide and 1-hydroxybenztriazole in a polar solvent, such as dimethylformamide, followed by the addition of hydroxylamine to the reaction mixture after a time period between about 15 minutes to about 1 hour, preferably about 30 minutes. The hydroxylamine is preferably generated in situ from a salt form, such as hydroxylamine hydrochloride, in the presence of a base, such as N-methylmorpholine. Alternatively, a protected derivative of hydroxylamine or its salt form, where the hydroxyl group is protected as a tert-butyl, benzyl or allyl ether, may be used in the presence of (benzotriazol-1-yloxy)tris(dimethylamino) phosphonium hexafluorophosphate and a base, such as N-methylmorpholine. Removal of the hydroxylamine protecting groups is carried out by hydrogenolysis with catalytic palladium on barium sulfate for a benzyl protecting group or treatment with a strong acid, such as trifluoroacetic acid, for a tert-butyl protecting group. The allyl protecting group may be removed by treatment with tributyltinhydride and acetic acid in the presence of catalytic bis (triphenylphosphine) palladium (II) chloride. N,O-bis(4-methoxybenzyl)hydroxylamine may also be used, when $R^{19}$ is $(C_1-C_6)$alkyl, as the protected hydroxylamine derivative where deprotection is achieved using a mixture of methanesulfonic acid and trifluoroacetic acid.

Compounds of the formula XV, wherein $R^{30}$ is hydrogen, are compounds of formula I, wherein X is $(C_1-C_6)$alkoxy.

The compound of formula of formula XV, wherein $R^{30}$ is hydrogen, is converted to the corresponding carboxylic acid compound of formula XVI by (a) saponification where $R^{19}$ is lower alkyl or (b) treatment with a strong acid, such as trifluoroacetic acid or hydrochloric acid, where $R^{19}$ is tert-butyl. Compounds of the formula XVI are compounds of the formula I wherein X is hydroxy.

Compounds of formula VII and X are commercially available or can be made by methods well known to those of ordinary skill in the art.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium slats.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where $R^3$ is hydrogen, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The ability of the compounds of formula I or their pharmaceutically acceptable salts (hereinafter also referred to as the compounds of the present invention) to inhibit matrix metalloproteinases or the production of tumor necrosis factor (TNF) and, consequently, demonstrate their effectiveness for treating diseases characterized by matrix metalloproteinase or the production of tumor necrosis factor is shown by the following in vitro assay tests.

BIOLOGICAL ASSAY

Inhibition of Human Collagenase (MMP-1)

Human recombinant collagenase is activated with trypsin using the following ratio: 10 mg trypsin per 100 mg of collagenase. The trypsin and collagenase are incubated at room temperature for 10 minutes then a five fold excess (50 mg10 mg trypsin) of soybean trypsin inhibitor is added.

10 mM stock solutions of inhibitors are made up in dimethyl sulfoxide and then diluted using the following Scheme:

10 mM→120 $\mu$M→12 $\mu$M→1.2 $\mu$M→0.12 $\mu$M

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D1-D6 and blanks (no enzyme, no inhibitors) are set in wells D7-D12.

Collagenase is diluted to 400 ng/ml and 25 ml is then added to appropriate wells of the microfluor plate. Final concentration of collagenase in the assay is 100 ng/ml.

Substrate (DNP-Pro-Cha-Gly-Cys(Me)-His-Ala-Lys (NMA)-NH$_2$) is made as a 5 mM stock in dimethyl sulfoxide and then diluted to 20 mM in assay buffer. The assay is initiated by the addition of 50 ml substrate per well of the microfluor plate to give a final concentration of 10 mM.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagenase containing samples (data from triplicate determinations is averaged). A time point that provides a good signal (the blank) and that is on a linear part of the curve (usually around 120 minutes) is chosen to determine IC$_{50}$ values. The zero time is used as a blank for each compound at each concentration and these values are subtracted from the 120 minute data. Data is plotted as inhibitor concentration vs % control (inhibitor fluorescence divided by fluorescence of collagenase alone ×100). IC$_{50}$'s are determined from the concentration of inhibitor that gives a signal that is 50% of the control.

If lC$_{50}$'s are reported to be <0.03 mM then the inhibitors are assayed at concentrations of 0.3 mM, 0.03 mM, 0.03 mM and 0.003 mM.

Inhibition of Gelatinase (MMP-2)

Inhibition of gelatinase activity is assayed using the Dnp-Pro-Cha-Gly-Cys(Me)-His-Ala-Lys(NMA)-NH$_2$ substrate (10 mM) under the same conditions as inhibition of human collagenase (MMP-1).

72 kD gelatinase is activated with 1 mM APMA (p-aminophenyl mercuric acetate) for 15 hours at 4° C. and is diluted to give a final concentration in the assay of 100 mg/ml. Inhibitors are diluted as for inhibition of human collagenase (MMP-1) to give final concentrations in the assay of 30 mM, 3 mM, 0.3 mM and 0.03 mM. Each concentration is done in triplicate.

Fluorescence readings (360 nm excitation, 460 emission) are taken at time zero and then at 20 minutes intervals for 4 hours.

$IC_{50}$'s are determined as per inhibition of human collagenase (MMP-1). If $IC_{50}$'s are reported to be less than 0.03 mM, then the inhibitors are assayed at final concentrations of 0.3 mM, 0.03 mM, 0.003 mM and 0.003 mM.

Inhibition of Stromelysin Activity (MMP-3)

Inhibition of stromelysin activity is based on a modified spectrophotometric assay described by Weingarten and Feder (Weingarten, H. and Feder, J., Spectrophotometric Assay for Vertebrate Collagenase, Anal. Biochem. 147, 437–440 (1985)). Hydrolysis of the thio peptolide substrate [Ac-Pro-Leu-Gly-SCH[$CH_2CH(CH_3)_2$]CO-Leu-Gly-$OC_2H_5$] yields a mercaptan fragment that can be monitored in the presence of Ellman's reagent.

Human recombinant prostromelysin is activated with trypsin using a ratio of 1 ml of a 10 mg/ml trypsin stock per 26 mg of stromelysin. The trypsin and stromelysin are incubated at 37° C. for 15 minutes followed by 10 ml of 10 mg/ml soybean trypsin inhibitor for 10 minutes at 37° C. for 10 minutes at 37° C. to quench trypsin activity.

Assays are conducted in a total volume of 250 ml of assay buffer (200 mM sodium chloride, 50 mM MES, and 10 mM calcium chloride, pH 6.0) in 96-well microliter plates. Activated stromelysin is diluted in assay buffer to 25 mg/ml. Ellman's reagent (3-Carboxy-4-nitrophenyl disulfide) is made as a 1M stock in dimethyl formamide and diluted to 5 mM in assay buffer with 50 ml per well yielding at 1 mM final concentration.

10 mM stock solutions of inhibitors are made in dimethyl sulfoxide and diluted serially in assay buffer such that addition of 50 mL to the appropriate wells yields final concentrations of 3 mM, 0.3 mM, 0.003 mM, and 0.0003 mM. All conditions are completed in triplicate.

A 300 mM dimethyl sulfoxide stock solution of the peptide substrate is diluted to 15 mM in assay buffer and the assay is initiated by addition of 50 ml to each well to give a final concentration of 3 mM substrate. Blanks consist of the peptide substrate and Ellman's reagent without the enzyme. Product formation was monitored at 405 nm with a Molecular Devices UVmax plate reader.

$IC_{50}$ values were determined in the same manner as for collagenase.

Inhibition of MMP-13

Human recombinant MMP-13 is activated with 2mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 mM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 mM, 3 mM, 0.3 mM, and 0.03 mM.

Substrate (Dnp-Pro-Cha-Gly-Cys(Me)-His-Ala-Lys (NMA)-$NH_2$) is prepared as for inhibition of human collagenase (MMP-1) and 50 ml is added to each well to give a final assay concentration of 10 mM. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If $IC_{50}$'s are reported to be less than 0.03 mM, inhibitors are then assayed at final concentrations of 0.3 mM, 0.03 mM, 0.003 mM and 0.0003 mM.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human mononuclear cells were isolated from anti-coagulated human blood using a one-step Ficoll-hypaque separation technique. (2) The mononuclear cells were washed three times in Hanks balanced salt solution (HBSS) with divalent cations and resuspended to a density of $2 \times 10^6$/ml in HBSS containing 1% BSA. Differential counts determined using the Abbott Cell Dyn 3500 analyzer ® indicated that monocytes ranged from 17 to 24% of the total cells in these preparations.

The cell suspension (180 mL) was aliquoted into flate bottom 96 well plates (Costar). Additions of compounds and LPS (100 ng/ml final concentration) gave a final volume of 200 ml. All conditions were performed in triplicate. After a four hour incubation at 37° C. in an humidified $CO_2$ incubator, plates were removed and centrifuged (10 minutes at approximately 250×g) and the supernatants removed and assayed for TNF using the R&D ELISA Kit.

The $IC_{50}$ values for Examples 1–4 are reported in Table 1, below

TABLE 1

| Example | MMP-13-$IC_{50}$(nM) | MMP-1 $IC_{50}$(nM) |
| --- | --- | --- |
| 1 | 10 | 80 |
| 1 | 12 | 145 |
| 2 | 1.7 | 195 |
| 2 | 3.5 | 300 |
| 2 | 2 | 200 |
| 3 | 20 | 4000 |
| 3 | 17 | 1300 |
| 4 | 52 | 800 |

As can be seen from the data reported in Table 1, above, the compounds of the invention possess a trend to MMP-13 selectivity.

For administration to humans for the inhibition of matrix metalloproteinases or the production of tumor necrosis factor (TNF), a variety of conventional routes may be used including orally, parenterally and topically. In general, the active compound will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The following Examples illustrate the preparation of the compounds of the present invention. Melting points are uncorrected. NMR data are reported in parts per million ($\delta$) and are referenced to the deuterium lock signal from the sample solvent (deuteriodimethylsulfoxide unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20 to 25° C. All non-aqueous reactions were run under a nitrogen atmosphere for convenience and to maximize yields. Concentration at reduced pressure means that a rotary evaporator was used.

EXAMPLE 1

3-[(4'-FLUOROBIPHENYL-4-SULFONYL)-(1-HYDROXYCARBAMOYLCYCLO-PENTYL) AMINO] PROPIONIC ACID METHYL ESTER (A) To a solution of 1-aminocyclopentanecarboxylic acid benzyl ester p-toluenesulfonic acid salt (12.1 grams, 30.9 mmol) and triethylamine (10.0 mL, 72 mmol) in water (150 mL) and 1,4-dioxane (150 mL) was added 4'-fluorobiphenyl-4-sulfonyl chloride (8.8 grams, 32.5 mmol). The mixture was stirred at room temperature for 16 hours and then most of the solvent was removed by evaporation under vacuum. The mixture was diluted with ethyl acetate and was washed successively with dilute hydrochloric acid solution, water, and brine. The solution was dried over magnesium sulfate and concentrated to leave 1-(4'-fluorobiphenyl-4-sulfonylamino)cyclopentanecarboxylic acid benzyl ester as a solid, 12.33 grams (76%).

(B) To a solution of 1-(4'-fluorobiphenyl-4-sulfonylamino)cyclopentanecarboxylic acid benzyl ester (23.0 grams, 50.7 mmol) in dry N,N-dimethylformamide (500 ml) at room temperature was added potassium hexamethyldisilazide (12.2 grams, 61.1 mmole) and, after 45 minutes, tert-butyl-(3-iodopropoxy)dimethylsilane (18.3 grams, 60.9 mmol). The resulting mixture was stirred at room temperature for 16 hours. Additional potassium hexamethyidisilazide (3.0 grams, 15 mmole) and tert-butyl-(3-iodopropoxy)-dimethylsilane (4.5 grams, 15 mmol) were then added. Stirring at room temperature was continued for a further 5 hours. The mixture was quenched by addition of saturated ammonium chloride solution. The N,N-dimethylformamide was removed by evaporation under vacuum. The residue was taken up in diethyl ether and washed successively with water, dilute aqueous hydrochloric acid solution and brine. After drying over magnesium sulfate, the diethyl ether was evaporated to afford a yellow oil. To this was added hexane and methylene chloride to induce crystallization of the starting material which was recovered by filtration. Evaporation of solvents from the filtrate afforded crude 1-[[3-(tert-butyl-dimethylsilanyloxy)propyl]-(4'-fluorobiphenyl-4-sulfonyl)amino]-cyclopentanecarboxylic acid benzyl ester as an amber oil (27.35 grams).

(C) To a solution of the crude 1-[[3-(tert-butyl-dimethylsilanyloxy)propyl]-(4'-fluorobiphenyl-4-sulfonyl)amino]cyclopentanecarboxylic acid benzyl ester (27.35 grams) in methylene chloride (450 mL) at room temperature was added boron trifluoride etherate (11 mL, 89.4 mmol). After 45 minutes, the reaction was quenched by sequential addition of saturated ammonium chloride solution and water. The organic phase was separated, washed with water and brine and dried over magnesium sulfate. Evaporation of the solvent under vacuum provided crude 1-[(4'-fluorobiphenyl-4-sulfonyl)-(3-hydroxypropyl)amino] cyclopentane carboxylic acid benzyl ester as an amber oil (22.1 grams).

(D) A solution of the crude 1-[(4'-fluorobiphenyl-4-sulfonyl)-(3-hydroxypropyl)amino]cyclopentanecarboxylic acid benzyl ester (22.1 grams) in acetone (400 mL) was cooled in an ice bath and treated with Jones reagent (about 20 mL) until an orange color persisted. The mixture was stirred from 0° C. to room temperature over 2 hours. After quenching excess oxidant with isopropanol (1 mL), Celite™ was added and the mixture was filtered. The filtrate was concentrated under vacuum. The residue was taken up in ethyl acetate, washed with water and brine, dried over magnesium sulfate and concentrated to afford crude 1-[(2-carboxyethyl)-( 4'-fluorobiphenyl-4-sulfonyl)amino]-cyclopentanecarboxylic acid benzyl ester as an oil (21.4 grams).

(E) To a solution of the crude 1-[(2-carboxyethyl)-(4'-fluorobiphenyl-4-sulfonyl)amino]-cyclopentanecarboxylic acid benzyl ester (21.4 grams) in N,N-dimethylformamide (500 mL) at room temperature was added potassium carbonate (22.5 grams, 163 mmole) and methyl iodide (3.7 mL, 59.4 mmole). The mixture was stirred for 16 hours at room temperature and was then concentrated under vacuum. The residue was taken up in water and acidified using 6N aqueous hydrogen chloride solution. The resulting mixture was extracted with a mixture of diethyl ether and ethyl acetate. The organic extract was washed with water and brine, dried over magnesium sulfate. After concentration to an amber oil, 1-[(4'-fluorobiphenyl-4-sulfonyl)-(2-methoxycarbonylethyl)amino]-cyclopentane-1-carboxylic acid benzyl ester (12.6 grams), a white solid, was isolated by flash chromatography on silica gel eluting with 15% ethyl acetate in hexane.

(F) A solution of 1-[(4'-fluorobiphenyl-4-sulfonyl)-(2-methoxycarbonylethyl)amino]-cyclopentane-1-carboxylic acid benzyl ester (12.1 grams, 22.4 mmole) in methanol (270 mL) was treated with 10% palladium on activated carbon and hydrogenated in a Parr™ shaker at 3 atmospheres pressure for 3.5 hours. After filtration through nylon (pore size 0.45 μm) to remove the catalyst, the solvent was evaporated to afford 1-[(4'-fluorobiphenyl-4-sulfonyl)-(2-methoxycarbonylethyl)amino]cyclopentane-1-carboxylic acid as a white foam (10.1 grams, 100%).

(G) Diisopropylethylamine (4.3 mL, 24.6 mmole) and (benzotriazol-1-yloxy)tris-(dimethylamino)phosphonium hexafluorophosphate (11.0 grams, 24.9 mmole) were added sequentially to a solution of 1-[(4'-fluorobiphenyl-4-sulfonyl)-(2-methoxycarbonylethyl)-amino]cyclopentane-1-carboxylic acid (10.1 grams, 22.4 mmole) in N,N-dimethylformamide (170 mL). The mixture was stirred for 4 hours. Additional diisopropylethylamine (7.8 mL, 44.6 mmole) and O-benzylhydroxylamine hydrochloride (4.64 grams, 29.1 mmole) were then added and the resulting mixture was stirred at 60° C. for 16 hours. After concentration under vacuum, the residue was taken up in water and acidified with 1 N aqueous hydrogen chloride solution. The mixture was extracted with ethyl acetate and the extract was washed sequentially with water, saturated aqueous sodium bicarbonate solution and brine. The solution was dried over magnesium sulfate and concentrated to give a solid which upon trituration with 7:3:1 hexane/ethyl acetate/methylene chloride provided 3-[(1-benzyloxycarbamoylcyclopentyl)-(4'-fluorobiphenyl-4-sulfonyl)amino]propionic acid methyl ester as a white crystalline solid (10.65 grams, 86%).

H) A solution of 3-[(1-benzyloxycarbamoylcyclopentyl)-(4'-fluorobiphenyl-4-sulfonyl)amino]propionic acid methyl ester (10.65 grams, 19.2 mmole) in methanol (250 mL) was treated with 5% palladium on barium sulfate and hydrogenated in a Parr™ shaker at 3 atmospheres pressure for 3 hours. After filtration through nylon (pore size 0.45 μm) to remove the catalyst, the solvent was evaporated to afford 3-[(4'-fluorobiphenyl-4-sulfonyl)-(1-hydroxycarbamoylcyclopentyl)amino]propionic acid methyl ester as a white foam (8.9 grams, 100%).

$^1$ H NMR (DMSO-d$_6$) δ 8.80 (br s, 1 H), 7.85–7.75 (m, 6 H), 7.32–7.25 (m, 2 H), 354 (s, 3 H), 3.52–3.48 (m, 2 H), 2.73–2.69 (m, 2 H), 2.24–2.21 (m, 2 H), 1.86–1.83 (m, 2 H 1.60 –1.40 (m, 4 H).

EXAMPLE 2

3-[(4'-FLUOROBIPHENYL-4-SULFONYL)-(1-HYDROXYCARBAMOYLCYCLO-PENTYL) AMINO] PROPIONIC ACID

A solution of 3-[(4'-fluorobiphenyl-4-sulfonyl)-(1-hydroxycarbamoylcyclopentyl)amino]-propionic acid methyl ester (8.9 grams, 19.2 mmole) in methanol (500 mL) was treated with aqueous 1 N sodium hydroxide solution (95 mL, 95 mmole) and stirred at room temperature for 5.5 hours. The mixture was concentrated to remove methanol, diluted with water, acidified with 6 N aqueous hydrochloric acid solution and extracted with ethyl acetate. After washing with water and brine the organic extract was dried over magnesium sulfate and concentrated to afford 3-[(4'-fluorobiphenyl-4-sulfonyl)-(1-hydroxycarbamoyl-cyclopentyl)amino]propionic acid as a white foam which was crystallized from ethyl acetate (6.74 grams, 78%).

Mp: 163–164° C. $^1$H NMR (DMSO-d$_6$) δ 12.30 (br s, 1 H), 10.40 (br s, 1 H), 8.77 (br s, 1 H), 7.89–7.74 (m, 6 H), 7.31–7.27 (m, 2 H), 3.51–3.44 (m, 2 H), 2.64–2.60 (m, 2 H), 2.24–2.22 (m, 2 H), 1.86–1.83 (m, 2 H), 1.60–1.40 (m, 4 H). MS 449 (M−1). Analysis calculated for $C_{21}H_{23}FN_2O_6S$: C, 55.99; H, 5.15; N, 6.22. Found: C, 55.69; H, 5.30; N, 6.18.

EXAMPLE 3

3-[(4'-FLUOROBIPHENYL-4-SULFONYL)-(1-HYDROXYCARBAMOYL-1-METHYL-ETHYL) AMINO]-PROPIONIC ACID ETHYL ESTER

The title compound was prepared according to a procedure analogous to that outlined in Example 1 starting with 2-amino-2-methyl-propionic acid benzyl ester p-toluenesulfonic acid salt and using ethyl iodide in place of methyl iodide in Step E.

MS (atmospheric pressure chemical ionization) acidic mode, 451 (M−1). $^1$H NMR (400 MHz, DMSO-d$_6$) δ 10.43 (s, 1 H), 8.80 (s,1 H), 7.96 (d, 2 H, J=8.5 Hz), 7.77–7.86 (m, 4 H), 7.31–7.35 (m, 2 H), 4.01 (q, 2 H, J=7.1 Hz), 3.31–3.43 (m, 2 H), 2.68–2.72 (m, 2 H), 1.44 (s, 6 H), 1.14 (t, 3 H, J=7.1 Hz). Analytical calculated for $C_{21}H_{25}FN_2O_6S$: C, 55.74; H, 5.57; N 6.19. Found: C, 55.59; H, 5.46; N, 6.28.

EXAMPLE 4

3-[(4'-FLUOROBIPHENYL-4-SULFONYL)-(1-HYDROXYCARBAMOYL-1-METHYL-ETHYL) AMINO]PROPIONIC ACID

The title compound was prepared from 3-[(4'-fluorobiphenyl-4-sulfonyl)-(1-hydroxycarbamoyl-1-methyl-ethyl)amino]-propionic acid ethyl ester according to a procedure analogous to that described in Example 2.

MS (atmospheric pressure chemical ionization) acidic mode, 423 (M−1). $^1$H NMR (400 MHz, DMSO-d$_6$) δ 10.4 (s,1 H), 8.76 (s,1 H), 7.94 (d, 2 H, J=8.7 Hz), 7.75–7.83 (m, 4 H), 7.27–7.32 (m, 2 H), 3.32–3.36 (m, 2 H), 2.58–2.62 (m, 2 H), 1.42 (s, 6 H).

What is claimed is:

1. A compound of the formula

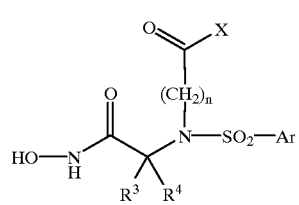

or the pharmaceutically acceptable salts thereof, wherein n is 1 to 6;

X is hydroxy, $(C_1-C_6)$alkoxy or $NR^1R^2$ wherein $R^1$ and $R^2$ are each independently selected from the group consisting of hydrogen, $(C_1-C_6)$alkyl, piperidyl, ($C_1$–$C_6$)alkylpiperidyl, ($C_6$–$C_{10}$)arylpiperidyl, ($C_2$–$C_9$)heteroarylpiperidyl, ($C_6$–$C_{10}$)aryl($C_1$–$C_6$)alkylpiperidyl, ($C_2$–$C_9$)heteroaryl($C_1$–$C_6$)alkylpiperidyl, ($C_1$–$C_6$)acylpiperidyl, ($C_6$–$C_{10}$)aryl, ($C_2$–$C_9$)heteroaryl, ($C_6$–$C_{10}$)aryl($C_1$–$C_6$)alkyl, ($C_2$–$C_9$)heteroaryl($C_1$–$C_6$)alkyl, ($C_6$–$C_{10}$)aryl ($C_6$–$C_{10}$)aryl, ($C_6$–$C_{10}$)aryl($C_6$–$C_{10}$)aryl($C_1$–$C_6$)alkyl, ($C_3$–$C_6$)cycloalkyl, ($C_3$–$C_6$)cycloalkyl($C_{1-6}$)alkyl, $R^5$($C_2$–$C_6$)alkyl, ($C_1$–$C_5$)alkyl(CHR$^5$)($C_1$–$C_6$)alkyl, wherein $R^5$ is hydroxy, ($C_1$–$C_6$)acyloxy, ($C_1$–$C_6$)alkoxy, piperazinyl, ($C_1$–$C_6$)acylamino, ($C_1$–$C_6$)alkylthio, ($C_6$–$C_{10}$)arylthio, ($C_1$–$C_6$)alkylsulfinyl, ($C_6$–$C_{10}$)arylsulfinyl, ($C_1$–$C_6$)alkylsulfoxyl, ($C_6$–$C_{10}$)arylsulfoxyl, amino, ($C_1$–$C_6$)alkylamino, (($C_{1-6}$)alkyl)$_2$amino, ($C_1$–$C_6$)acylpiperazinyl, ($C_1$–$C_6$)alkylpiperazinyl, ($C_6$–$C_{10}$)aryl($C_1$–$C_6$)alkylpiperazinyl, ($C_2$–$C_9$)heteroaryl($C_{1-6}$)alkylpiperazinyl, morpholinyl, thiomorpholinyl, piperidinyl or pyrrolidinyl; $R^6$($C_1$–$C_6$)alkyl, ($C_1$–$C_5$)alkyl(CHR$^6$)($C_1$–$C_6$)alkyl, wherein $R^6$ is piperidyl, ($C_1$–$C_6$)alkylpiperidyl, ($C_6$–$C_{10}$)arylpiperidyl, ($C_6$–$C_{10}$)aryl($C_1$–$C_6$)alkylpiperidyl, ($C_2$–$C_9$)heteroarylpiperidyl or ($C_2$–$C_9$)heteroaryl($C_1$–$C_6$)alkylpiperidyl; and CH($R^7$)COR$^8$, wherein $R^7$ is hydrogen, ($C_1$–$C_6$)alkyl, ($C_6$–$C_{10}$)aryl($C_1$–$C_6$)alkyl, ($C_2$–$C_9$)heteroaryl($C_1$–$C_6$)alkyl, ($C_1$–$C_6$)alkylthio($C_1$–$C_6$)alkyl, ($C_6$–$C_{10}$)arylthio($C_1$–$C_6$)alkyl, ($C_1$–$C_6$)alkylsulfinyl($C_1$–$C_6$)alkyl, ($C_6$–$C_{10}$)arylsulfinyl($C_1$–$C_6$)alkyl, ($C_1$–$C_6$)alkylsulfonyl($C_1$–$C_6$)alkyl, ($C_6$–$C_{10}$)arylsulfonyl($C_1$–$C_6$)alkyl, hydroxy($C_1$–$C_6$)alkyl, amino($C_1$–$C_6$)alkyl, ($C_1$–$C_6$)alkylamino($C_1$–$C_6$)alkyl, (($C_1$–$C_6$)alkyl)$_2$amino($C_1$–$C_6$)alkyl, $R^9R^{10}$NCO($C_1$–$C_6$)alkyl or $R^9$OCO($C_1$–$C_6$)alkyl, wherein $R^9$ and $R^{10}$ are each independently selected from the group consisting of hydrogen, ($C_1$–$C_6$)alkyl, ($C_6$–$C_{10}$)aryl($C_1$–$C_6$)alkyl and ($C_2$–$C_9$)heteroaryl($C_1$–$C_6$)alkyl; and $R^8$ is $R^{11}$O or $R^{11}R^{12}$N, wherein $R^{11}$ and $R^{12}$ are each independently selected from the group consisting of hydrogen, ($C_1$–$C_6$)alkyl, ($C_6$–$C_{10}$)aryl($C_1$–$C_6$)alkyl and ($C_2$–$C_9$)heteroaryl($C_1$–$C_6$)alkyl;

or $R^1$ and $R^2$, or $R^9$ and $R^{10}$, or $R^{11}$ and $R^{12}$ may be taken together to form an azetidinyl, pyrrolidinyl, morpholinyl, thiomorpholinyl, indolinyl, isoindolinyl, piperazinyl, tetrahydroquinolinyl, tetrahydroisoquinolinyl, ($C_1$–$C_6$)acylpiperazinyl, ($C_1$–$C_6$)alkylpiperazinyl, ($C_6$–$C_{10}$)arylpiperazinyl, ($C_2$–$C_9$)heteroarylpiperazinyl or a bridged diazabicycloalkyl ring selected from the group consisting of

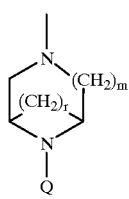

a

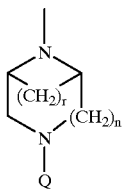

b

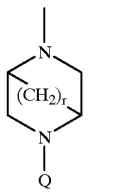

c

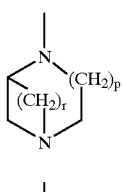

d

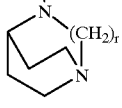

e wherein r is 1, 2 or 3;
m is 1 or 2;
p is 0 or 1;
Q is hydrogen, ($C_1$–$C_3$)alkyl or ($C_1$–$C_6$)acyl;
$R^3$ and $R^4$ are each independently selected from the group consisting of hydrogen, ($C_1$–$C_6$)alkyl, trifluoromethyl, trifluoromethyl($C_1$–$C_6$)alkyl, ($C_1$–$C_6$)alkyl(difluoromethylene), ($C_1$–$C_3$)alkyl(difluoromethylene)($C_1$–$C_3$)alkyl, ($C_6$–$C_{10}$)aryl, ($C_2$–$C_9$)heteroaryl, ($C_6$–$C_{10}$)aryl($C_1$–$C_6$)alkyl, ($C_2$–$C_9$)heteroaryl($C_1$–$C_6$)alkyl, ($C_6$–$C_{10}$)aryl ($C_6$–$C_{10}$)aryl, ($C_6$–$C_{10}$)aryl($C_6$–$C_{10}$)aryl($C_1$–$C_6$)alkyl, ($C_3$–$C_6$)cycloalkyl, ($C_3$–$C_6$)cycloalkyl($C_1$–$C_6$)alkyl, hydroxy($C_1$–$C_6$)alkyl, ($C_{1-6}$)acyloxy($C_1$–$C_6$)alkyl, ($C_1$–$C_6$)alkoxy($C_1$–$C_6$)alkyl, piperazinyl($C_1$–$C_6$)alkyl, ($C_1$–$C_6$)acylamino($C_1$–$C_6$)alkyl, piperidyl, ($C_1$–$C_6$)alkylpiperidyl, ($C_6$–$C_{10}$)aryl($C_1$–$C_6$)alkoxy($C_1$–$C_6$)alkyl, ($C_2$–$C_9$)heteroaryl($C_1$–$C_6$)alkoxy($C_1$–$C_6$)alkyl, ($C_1$–$C_6$)alkylthio($C_1$–$C_6$)alkyl, ($C_6$–$C_{10}$)arylthio($C_1$–$C_6$)alkyl, ($C_1$–$C_6$)alkylsulfinyl($C_1$–$C_6$)alkyl, ($C_6$–$C_{10}$)arylsulfinyl($C_1$–$C_6$)alkyl, ($C_1$–$C_6$)alkylsulfonyl($C_1$–$C_6$)alkyl, ($C_6$–$C_{10}$)arylsulfonyl($C_1$–$C_6$)alkyl, amino($C_1$–$C_6$)alkyl, ($C_1$–$C_6$)alkylamino($C_1$–$C_6$)alkyl, (($C_1$–$C_6$)alkyl)$_2$amino($C_1$–$C_6$)alkyl, $R^{13}$CO($C_1$–$C_6$)alkyl wherein $R^{13}$ is $R^{20}$O or $R^{20}R^{21}$N wherein $R^{20}$ and $R^{21}$ are each independently selected from the group consisting of hydrogen, ($C_1$–$C_6$)alkyl, ($C_6$–$C_{10}$)aryl($C_1$–$C_6$)alkyl or ($C_2$–$C_9$)heteroaryl($C_{1-6}$)alkyl; or $R^{14}$($C_1$–$C_6$)alkyl wherein $R^{14}$ is ($C_1$–$C_6$)acylpiperazinyl, ($_6$–$C_{10}$)arylpiperazinyl, ($C_2$–$C_9$)heteroarylpiperazinyl, ($C_1$–$C_6$)alkylpiperazinyl, ($C_6$–$C_{10}$)aryl($C_1$–$C_6$)alkylpiperazinyl, ($C_2$–$C_9$)heteroaryl($C_1$–$C_6$)alkylpiperazinyl, morpholinyl, thiomorpholinyl, piperidinyl, pyrrolidinyl, piperidyl, $(C_1-C_6)$ alkylpiperidyl, $(C_6-C_{10})$arylpiperidyl, $(C_2-C_9)$ heteroarylpiperidyl, $(C_6-C_{10})$aryl$(C_1-C_6)$ alkylpiperidyl, $(C_2-C_9)$heteroaryl$(C_1-C_6)$ alkylpiperidyl or $(C_1-C_6)$acylpiperidyl;

or $R^3$ and $R^4$, or $R^{20}$ and $R^{21}$ may be taken together to form a $(C_3-C_6)$cycloalkyl, oxacyclohexyl, thiocyclohexyl, indanyl or tetralinyl ring or a group of the formula

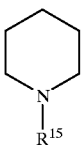

wherein $R^{15}$ is hydrogen, $(C_1-C_6)$acyl, $(C_1-C_6)$ alkyl, $(C_6-C_{10})$aryl$(C_1-C_6)$alkyl, $(C_2-C_9)$heteroaryl $(C_1-C_6)$alkyl or $(C_1-C_6)$alkylsulfonyl; and Ar is $(C_6-C_{10})$aryl$(C_6-C_{10})$aryl;

with the proviso that when either $R^1$ or $R^2$ is CH($R^7$) COR$^8$ wherein $R^7$ and $R^8$ are as defined above, the other of $R^1$ or $R^2$ is hydrogen, $(C_{1-6})$alkyl or benzyl.

2. A compound according to claim 1, wherein n is 2.

3. A compound according to claim 1, wherein Ar is 4-fluorophenyl-phenyl, 4-chlorophenyl-phenyl or phenyl-phenyl.

4. A compound according to claim 1, wherein either $R^3$ or $R^4$ is not hydrogen.

5. A compound according to claim 1, wherein n is 1, X is NR$^1$R$^2$ and either $R^1$ or $R^2$ is not hydrogen.

6. A compound according to claim 1, wherein X is hydroxy, Ar is 4-fluorophenyl-phenyl, phenyl-phenyl or 4-chlorophenyl-phenyl and either $R^3$ or $R^4$ is not hydrogen.

7. A compound according to claim 1, wherein X is alkoxy, Ar is 4-fluorophenyl-phenyl, phenyl-phenyl or 4-chlorophenyl-phenyl and either $R^3$ or $R^4$ is not hydrogen.

8. A compound according to claim 1, wherein Ar is 4-fluorophenyl-phenyl, phenyl-phenyl or 4-chlorophenyl-phenyl and $R^3$ and $R^4$ are taken together to form $(C_3-C_6)$ cycloalkanyl, oxacyclohexanyl, thiocyclohexanyl, indanyl or a group of the formula

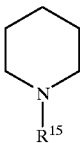

wherein $R^{15}$ is $(C_1-C_6)$acyl, $(C_1-C_6)$alkyl, $(C_6-C_{10})$aryl $(C_1-C_6)$alkyl, $(C_2-C_9)$heteroaryl$(C_1-C_6)$alkyl or $(C_1-C_6)$alkylsulfonyl.

9. A compound according to claim 1, wherein Ar is 4-fluorophenyl-phenyl, phenyl-phenyl or 4-chlorophenyl-phenyl and $R^3$ and $R^4$ are each $(C_1-C_6)$alkyl.

10. A compound according to claim 2, wherein X is hydroxy or $(C_1-C_6)$alkoxy.

11. A compound according to claim 3, wherein X is hydroxy or $(C_1-C_6)$alkoxy.

12. A compound according to claim 4, wherein X is hydroxy or $(C_1-C_6)$alkoxy.

13. A compound according to claim 8, wherein X is hydroxy or $(C_1-C_6)$alkoxy.

14. A compound according to claim 9, wherein X is hydroxy or $(C_1-C_6)$alkoxy.

15. A compound according to claim 1, wherein X is NR$^1$R$^2$ and $R^1$ and $R^2$ are taken together to form a heterocycle selected from piperazinyl and morpholinyl.

16. A compound according to claim 2, wherein X is NR$^1$R$^2$ and $R^1$ and $R^2$ are taken together to form a heterocycle selected from piperazinyl and morpholinyl.

17. A compound according to claim 3, wherein X is NR$^1$R$^2$ and $R^1$ and $R^2$ are taken together to form a heterocycle selected from piperazinyl and morpholinyl.

18. A compound according to claim 4, wherein X is NR$^1$R$^2$ and $R^{and\ R2}$ are taken together to form a heterocycle selected from piperazinyl and morpholinyl.

19. A compound according to claim 8, wherein X is NR$^1$R$^2$ and $R^1$ and $R^2$ are taken together to form a heterocycle selected from piperazinyl and morpholinyl.

20. A compound according to claim 9, wherein X is NR$^1$R$^2$ and $R^1$ and $R^2$ are taken together to form a heterocycle selected from piperazinyl and morpholinyl.

21. A compound according to claim 1, wherein said compound is selected from the group consisting of:
 3-[(4'-fluorobiphenyl-4-sulfonyl)-(1-hydroxycarbamoylcyclopentyl)amino] propionic acid methyl ester,
 3-[(4'-fluorobiphenyl-4-sulfonyl)-(1-hydroxycarbamoylcyclopentyl)amino] propionic acid,
 3-[(4'-fluorobiphenyl-4-sulfonyl)-(1-hydroxycarbamoyl-1-methyl-ethyl)amino]-propionic acid ethyl ester, and
 3-[(4'-fluorobiphenyl-4-sulfonyl)-(1-hydroxycarbamoyl-1-methyl-ethyl)amino]propionic acid.

22. A pharmaceutical composition for (a) the treatment of a condition selected from the group consisting of arthritis, cancer, tissue ulceration, restenosis, periodontal disease, epidermolysis bullosa, scleritis, bone resorption, loosening of artificial joint implants, atherosclerosis, multiple sclerosis, occular angiogenisis and other diseases characterized by matrix metalloproteinase activity, AIDS, sepsis, septic shock and other diseases involving the production of tumor necrosis factor (TNF) or (b) the inhibition of matrix metalloproteinases or the production of tumor necrosis factor (TNF) in a mammal, including a human, comprising an amount of a compound of claim 1 or a pharmaceutically acceptable salt thereof, effective in such treatments or inhibition and a pharmaceutically acceptable carrier.

23. A method for the inhibition of (a) matrix metalloproteinases or (b) the production of tumor necrosis factor (TNF) in a mammal, including a human, comprising administering to said mammal an effective amount of a compound of claim 1 or a pharmaceutically acceptable salt thereof.

24. A method for treating a condition selected from the group consisting of arthritis, cancer, tissue ulceration, restenosis, periodontal disease, epidermolysis bullosa, scleritis, bone resorption, loosening of artificial joint implants, atherosclerosis, multiple sclerosis, occular angiogenisis and other diseases characterized by matrix metalloproteinase activity, AIDS, sepsis, septic shock and other diseases involving the production of tumor necrosis factor (TNF) in a mammal, including a human, comprising administering to said mammal an amount of a compound of claim 1 or a pharmaceutically acceptable salt thereof, effective in treating such a condition.

* * * * *